United States Patent [19]

Pless et al.

[11] 4,247,543
[45] Jan. 27, 1981

[54] ORGANIC COMPOUNDS

[75] Inventors: Janos Pless, Basel; Edmond Sandrin, Rhine, both of Switzerland

[73] Assignee: Sandoz Ltd., Basel, Switzerland

[21] Appl. No.: 28,603

[22] Filed: Apr. 9, 1979

Related U.S. Application Data

[63] Continuation of Ser. No. 816,825, Jul. 18, 1977, abandoned.

[51] Int. Cl.³ .................... A61K 37/00; C07C 103/52
[52] U.S. Cl. ............................. 424/177; 260/112.5 R
[58] Field of Search .................. 424/177; 260/112.5 R

[56] References Cited
U.S. PATENT DOCUMENTS 4,128,541  12/1978  Sarantakis et al. .................. 424/177

FOREIGN PATENT DOCUMENTS 2703109  4/1977  Fed. Rep. of Germany .... 260/112.5 R

OTHER PUBLICATIONS

D. Roemer et al., Nature 268, 1977, 547–549.

*Primary Examiner*—Delbert R. Phillips
*Attorney, Agent, or Firm*—Gerald D. Sharkin; Robert S. Honor; Thomas O. McGovern

[57] ABSTRACT

The invention provides polypeptides of the formula,

A-B-Gly-D-E-F wherein
A is Tyr or substituted Tyr,
B is, for example, -Gly-, -(D)-Ala-, or -(D)-Met-,
D is Phe or substituted Phe,
E is, for example, -Leu-, -Nle-, -Nva-, -Ile- or -Val-,
and F is $-NR_7CHR_8CH_2OR_3'$,
  wherein, for example, $R_3'$ may be hydrogen or alkyl—CO—, $R_7$ is hydrogen or alkyl and $R_8$ is alkyl, which compounds possess pharmacological activity, for example, analgesic activity.

16 Claims, No Drawings

ORGANIC COMPOUNDS

This is a continuation of application Ser. No. 816,825 filed July 18, 1977, now abandoned.

The present invention relates to polypeptide derivatives.

More particularly, the present invention provides compounds of formula I, $$A\text{-}B\text{-}Gly\text{-}D\text{-}E\text{-}F \qquad I$$

wherein A is a residue of formula

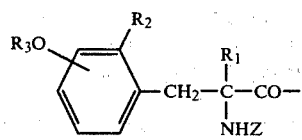

wherein
$R_1$ is hydrogen or alkyl of 1 to 4 carbon atoms,
$R_2$ is hydrogen or, together with $R_1$, forms an ethylene bridge, and
$R_3$ is hydrogen, alkyl of 1 to 4 carbon atoms or an $R_4CO$- group,
  wherein $R_4$ is a saturated or unsaturated branched or unbranched alkyl residue of 1 to 17 carbon atoms, phenyl or phenylalkyl of 7 to 12 carbon atoms in which the phenyl residue can be mono- or di-substituted with fluorine, chlorine or bromine, alkyl of 1 to 4 carbon atoms or alkoxy of 1 to 4 carbon atoms, whereby the $R_3O$ group is in a position meta- or para- to the

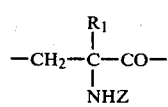

residue,
Z is hydrogen, alkyl of 1 to 5 carbon atoms, alkenyl of 3 to 5 carbon atoms, cyclopropylmethyl, cyclobutylmethyl, $R_4CO$—, wherein $R_4$ is as previously defined, or a residue of a natural L-amino acid or of a dipeptide formed from natural amino acids, whereby instead of a natural L-amino acid, methioninesulphoxide or methioninesulphone, may be used,
B is -Gly-, -(D)-Ala-, -(D)-Met-, (D)-methioninesulphoxide or (D)-methioninesulphone, (D)-S-methylcystein, (D)-methylcysteinsulphoxide or (D)-S-methylcystein-sulphone,
D is a residue of formula

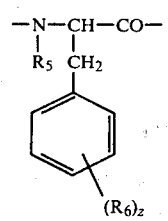

wherein
$R_5$ is hydrogen or alkyl of 1 to 4 carbon atoms,
$R_6$ is hydrogen, fluorine, chlorine, bromine, nitro, alkyl of 1 to 4 carbon atoms or alkoxy of 1 to 4 carbon atoms, and z is 1 or 2,
E is -Leu-, -Nle-, -Nva-, -Ile-, -Val- or

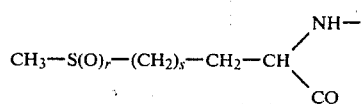

wherein
r is 0, 1 or 2 and
s is 0, 1 or 2,
and F is (1°) a residue of formula

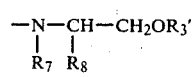

wherein $R_3'$ is hydrogen or $R_4CO$—, wherein $R_4$ is as previously defined,
$R_7$ is hydrogen or alkyl of 1 to 4 carbon atoms, and
$R_8$ is
(a)

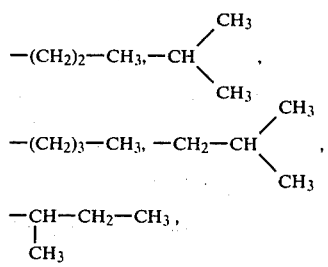

(b) —$(CH_2)_m$—$CH_2OR_3'$
wherein
$R_3'$ is as previously defined, and
m is from 0 to 6,

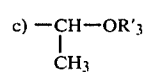

wherein
$R_3'$ is as previously defined,
(d) -$CH_2$-S-H,
(e)

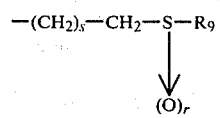

wherein
$R_9$ is alkyl of 1 to 5 carbon atoms,
r is 0, 1 or 2, and
s is 0, 1 or 2,
(f)    —$(CH_2)_4$—$NH_2$,    —$(CH_2)_4$—$NHCOR_4$,
wherein $R_4$ is as previously defined,

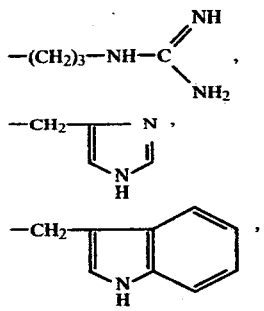

(g) —(CH$_2$)$_n$—CONH$_2$, wherein n is 1 or 2,
(h) —(CH$_2$)$_n$—COOR$_{10}$,
  wherein
  n is as previously defined, and
  R$_{10}$ is hydrogen or alkyl of 1 to 5 carbon atoms, or
(i) together with R$_7$ is —(CH$_2$)$_3$—,
or (2°) a residue of formula

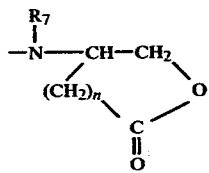

wherein n and R$_7$ are as previously defined,
whereby the A, D and E residues possess either the L- or D,L- configuration and the residue F possesses the L-, D- or D,L- configuration.

When R$_1$ is alkyl, this is preferably methyl. R$_1$ preferably is hydrogen, or, together with R$_2$, forms an ethylene bridge.

When R$_3$ is alkyl, this is preferably methyl.
R$_3$ especially signifies hydrogen.
R$_3$O is preferably in a position para- to the

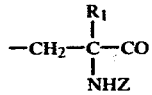

residue.

When Z is alkyl, this is preferably methyl. When Z is a natural amino acid, this is preferably H-Arg-, H-Lys-, H-Phe-, H-Tyr- or H-Ala-. Z is preferably hydrogen, alkyl, a natural amino acid or a dipeptide.

B is preferably -(D)-Ala-, (D)-Met-, (D)-methioninesulphoxide or (D)-methioninesulphone.

When R$_5$ is alkyl, this is preferably methyl. R$_5$ is preferably methyl or hydrogen.

R$_6$ is preferably hydrogen, nitro or chlorine, especially hydrogen or nitro.

As an amino acid residue, E is preferably methionine, methioninesulphoxide or methioninesulphone, especially methioninesulphoxide.

R$_7$ is especially hydrogen.
R$_3$' is preferably hydrogen.
R$_9$ is preferably methyl.
r is preferably 1 or 2, especially 1.
s is preferably 0 or 1, especially 1.
n is preferably 2.

F is preferably serinol, asparaginol or threoninol. F preferably has the L-configuration.

In one group of compounds, R$_4$ is alkyl of 1 to 17 carbon atoms, suitably 1 to 12 carbon atoms, conveniently from 1 to 6 carbon atoms, for example, methyl, ethyl, propyl and butyl. When R$_4$ is alkyl of two or more carbon atoms, this moiety may be unsaturated.

When R$_4$ is phenyl or phenylalkyl of 7 to 12 carbon atoms, e.g. tolyl or benzyl, the phenyl residue may be mono- or di-substituted with fluorine, chlorine or bromine. The phenyl residue may also be substituted with alkyl of 1 to 4 carbon atoms or alkoxy of 1 to 4 carbon atoms.

In a second group of compounds, Z is hydrogen, alkyl of 1 to 5 carbon atoms, alkenyl of 3 to 5 carbon atoms, cyclopropylmethyl or cyclobutylmethyl.

In a third group of compounds, Z is R$_4$CO, wherein R$_4$ is as previously defined.

In a fourth group of compounds, R$_6$ is hydrogen, fluorine, chlorine, bromine or nitro.

In a fifth group of compounds, R$_6$ is alkyl of 1 to 4 carbon atoms or alkoxy of 1 to 4 carbon atoms.

In a sixth group of compounds, E is -Leu-, -Nle-, -Nva-, -Ile- or -Val-. In another group of compounds, E is

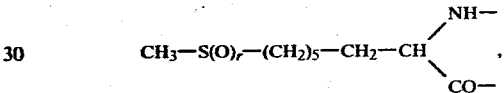

wherein r and s are as previously defined.

In a seventh group of compounds, F as previously defined under (i) is

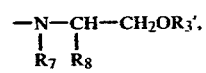

wherein R$_3$' and R$_7$ are as previously defined and R$_8$ is as previously defined under (a), (b) and (c). In another group of compounds, R$_8$ is as previously defined under (d) and (e). In a further group of compounds, R$_8$ is —(CH$_2$)$_4$—NH$_2$, —(CH$_2$)$_4$—NHCOR$_4$, wherein R$_4$ is as previously defined, or R$_8$ is as previously defined under (g), (h) and (i). In three further groups of compounds, R$_8$ is

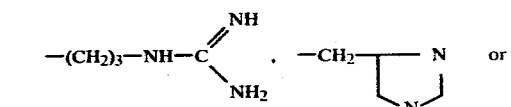

In an eighth group of compounds, F is as previously defined under (2°).

A peptide of formula I may be obtained by methods which are conventional in the art of peptide synthesis.

Accordingly, the present invention provides a process for the production of a peptide of formula I which comprises (a) removing at least one protective group from a protected peptide having the sequence indicated in formula I, or (b) linking together by an amide bond two peptide units, each of which contains at least one amino acid and which is in protected or unprotected form, the peptide units being such that the amino acid sequence given in formula I is obtained, and then, if necessary, effecting process variant (a), or (c) converting a group A, B, E and/or F of an unprotected or protected peptide into another group A, B, E and/or F having the definition previously indicated, and, if necessary, effecting process variant (a).

The above methods are known in peptide chemistry and may be effected in manner analogous to the processes described in the following Examples.

Insofar as the production of the starting materials is not particularly described, these compounds are known or may be produced and purified in accordance with known methods. These compounds may also be produced in a manner analogous to the processes described in the following Examples.

The compounds may exist in salt, including acid addition salt, forms or in the form of complexes, for example, complexes with metals.

Suitable metals for complex formation include calcium, magnesium, aluminium, cobalt and especially zinc.

In the following Examples, all temperatures are indicated in degrees Celsius.

The following abbreviations are used:
Ac=acetyl
Boc=tert.-butyloxycarbonyl
Bzl=benzyl
CBO=benzyloxycarbonyl
DMF=dimethylformamide
Me=methyl
MePhe=N-methylphenylalanine
TFA=trifluoroacetic acid
decomp.=decomposition temperature
THF=tetrahydrofuran
Asn-ol=asparaginol.

EXAMPLE 1

H-Tyr-(D)-Ala-Gly-Phe-Met-serinol (trifluoroacetate)

2 g of Boc-Tyr-(D)-Ala-Gly-Phe-Met-serinol are dissolved at room temperature in 10 ml of $CF_3COOH/CH_2Cl_2$ (1:1 v/v). After 30 minutes, the mixture is concentrated under vacuum and the residue triturated with ether. The solid product is recrystallized from methanol/ether to yield the title compound. M.P. 200° (decomp.). $[\alpha]_D^{20} = +2.1°$ (C=1.0 in DMF).

The Boc-Tyr-(D)-Ala-Gly-Phe-Met-serinol employed as starting material is produced as follows:

(a) Boc-Tyr-(D)-Ala-Gly-Phe-$OCH_3$ 53 g of CBO-(D)-Ala-Gly-Phe-$OCH_3$ are dissolved in 400 ml of dioxane and 50 ml of water after the addition of 5 g of a platinum catalyst and hydrogenated at room temperature under normal pressure until no further hydrogen is absorbed. The catalyst is filtered off, the mixture concentrated and the residue taken up in 200 ml of DMF. 15 g of hydroxysuccinimide, 30 g of Boc-Tyrosine and 26 g of dicyclohexylcarbodiimide are added to the solution at 0° C. After one day at 0° C. and one day at room temperature, the dicyclohexyl urea which separates out if filtered off and the filtrate concentrated and taken up in ethyl acetate. The mixture is washed with dilute HCl and water and concentrated. On adding ether, the title product crystallizes out of the concentrated solution. M.P. 100° (decomp.). $[\alpha]_D^{20} = -9.5$ (C=1 in DMF).

(b) Boc-Tyr-(D)-Ala-Gly-Phe-$NHNH_2$ 43 g of Boc-Tyr-(D)-Ala-Gly-Phe-$OCH_3$ are dissolved in 300 ml of methanol and 35 ml of hydrazine hydrate are added. After one day at room temperature, the mixture is evaporated and the residue is triturated with water which has been acidified to pH 3 with HCl. The precipitated product is filtered and dried to yield the title compound. M.P. 195° (decomp.). $[\alpha]_D^{20} = -20.9$ (C=1 in DMF).

(c) Boc-Tyr-(D)-Ala-Gly-Phe-Met-serinol

To 2.5 g of Boc-Tyr-(D)-Ala-Gly-Phe-$NHNH_2$ in 40 ml of DMF are added 2.7 ml of 5.6 N HCl in dioxane and 0.52 ml of tert.butylnitrite at −20° and, after 10 minutes, 3.4 ml of triethylamine and 2 g of H-Met-serinol trifluoroacetate. After 4 hours at 0° and 15 hours at room temperature, the mixture is concentrated under vacuum, the residue taken up in ethyl acetate and washed repeatedly with dilute HCl and water and the organic phase evaporated. The residue crystallizes from methanol/ether to yield the title compound. M.P. 140° (decomp.). $[\alpha]_D^{20} = -15$ (C=1 in DMF).

EXAMPLE 2

H-Tyr-(D)-Ala-Gly-Phe-methioninesulphoxide-serinol (trifluoroacetate)

To a solution of 1 g of H-Tyr-(D)-Ala-Gly-Phe-Met-serinol (trifluoroacetate) in 10 ml of water are added 1.8 ml of a 0.1 N solution of hydrogen peroxide. After one hour at room temperature, the solution is lyophilised to yield the title compound. M.P. 225° (decomp.). $[\alpha]_D^{20} = +0.3°$ (C=1 in DMF).

EXAMPLE 3

H-Tyr-(D)-Ala-Gly-MePhe-Leu-Asn-ol (hydrochloride)

0.88 g of CBO-Tyr(Bzl)-(D)-Ala-Gly-MePhe-Leu-Asn-ol are dissolved, with one equivalent of aqueous hydrochloric acid, in 40 ml of acetic acid/water (8:2 v/v), 100 mg of Pd (10% on active charcoal) are added and hydrogenation effected at normal pressure and room temperature. After 4 hours, the catalyst is filtered off, the solvent removed under vacuum and the residue triturated with ether to yield the title compound. $[\alpha]_D^{20} = -10.7°$ (C=0.97 in $CH_3COOH$ 95%).

The CBO-Tyr(Bzl)-(D)-Ala-Gly-MePhe-Leu-Asn-ol is prepared as follows:

(a) Boc-MePhe-Leu-OMe

To a solution of 28 g of Boc-MePhe-OH and 11.2 ml of N-methylmorpholine in 400 ml of THF are added 13.2 ml of chloroformic acid isobutyl ester at −25°. After 5 minutes, at −25°, 18 g of HCl-Leu-OMe and 11.2 ml of N-methylmorpholine in 200 ml of DMF are added to the solution. After 2 hours, at −15°, the mixture is diluted with ethylacetate, washed with dilute aqueous $KHCO_3$ solution, hydrochloric acid, water, dried and the solvent removed under vacuum to yield the title compound as a viscous oil.

(b) Boc-(D)-Ala-Gly-MePhe-Leu-OMe

To a solution of 24.6 g of Boc-(D)-Ala-Gly-OH and 11.2 ml of N-methylmorpholine in 400 ml of THF are added 13.2 ml of chloroformic acid isobutyl ester at −25°. After 5 minutes, at 25°, 11.2 ml of N-methyl-morpholine and 42.1 g of H-MePhe-Leu-OMe (trifluoroacetate) in DMF [which has previously been prepared by the treatment of Boc-MePhe-Leu-OMe with TFA-methylene chloride (1:1)] are added. After 2 hours, at −15°, the title compound is isolated as described under (a) above, as a solid foam.

(c) CBO-Tyr(Bzl)-(D)-Ala-Gly-MePhe-Leu-OMe

To a solution of 4.1 g of CBO-Tyr(Bzl)-OH and 1.1 ml of N-methylmorpholine in 40 ml of THF are added 1.3 ml of chloroformic acid isobutyl ester at −25° are added a solution of 1.1 ml of N-methylmorpholine and 5.5 g of H-(D)-Ala-Gly-MePhe-Leu-OMe (trifuloroacetate) in 20 ml of DMF [previously produced by treatment of Boc-(D)-Ala-Gly-MePhe-Leu-OMe with TFA-methylene chloride]. After 2 hours at −15°, the isolation described under (a) above is effected to yield the title compound as a solid foam.

(d) CBO-Tyr(Bzl)-(D)-Ala-Gly-MePhe-Leu-NHNH$_2$ 7.6 g of CBO-Tyr(Bzl)-(D)-Ala-Gly-MePhe-Leu-OMe and 5 ml of hydrazine hydrate are dissolved in methanol. After 6 hours at 0°, the product is precipitated by the addition of water. The product is washed with a large quantity of water to remove the base to yield the title compound. M.P. 96° (decomp.). $[\alpha]_D^{20} = -29.6$ (C=1.0 in DMF).

(e) CBO-Tyr(Bzl)-(D)-Ala-Gly-MePhe-Leu-Asn-ol

To 7.6 g of CBO-Tyr(Bzl)-(D)-Ala-Gly-MePhe-Leu-NHNH$_2$ in 40 ml of DMF are added, at −30°, 5.4 ml of 5.6 N HCl in dioxane, 1.2 ml of tert.-butylnitrite and, after 10 minutes, 6.7 ml of N-methylmorpholine and 1.5 g of asparaginol hydrochloride. After 15 hours at 0°, the mixture is concentrated under vacuum. The residue is taken up in ethyl acetate, hydrochloric acid and water, and the organic phase evaporated. The raw product is purified by column chromatography on kieselgel. Elution is effected with a mixture of methylene chloride/methanol to yield the title compound. M.P. 103° (decomp.). $[\alpha]_D^{20} = 32.5$ (C=1.0 in DMF).

The following compounds can be prepared in manner analogous to those described in Examples 1, 2 or 3 using appropriate starting materials in approximately equivalent amounts.

[All amino acid residues with the exception of glycyl, as well as all the amino alcohols with the exception of serinol, have, unless otherwise stated, the L-configuration. An amino alcohol is assigned to the L-series if the —CH$_2$—OH group occupies the position of the α-COOH group in the corresponding L-amino acid. In the case of a lactone defined under F 2°) (Examples 5 and 11), the series to which this belongs is resolved after hydrolytic opening of the lactone ring.]

their high affinity for the opiate receptors in rat brains as indicated by the method of C. B. Pert and S. H. Snyder [Molecular Pharmacology 10, 868 (1974)] and also in the Tail Flick Test in mice on i.v. administration of from 1 to about 50 mg/kg of animal body weight of the compounds.

Additionally, observations in mice show that the compounds of formula I inhibit spontaneous motor activity in mice on s.c. and p.o. administration of from about 1.0 to about 100 mg/kg animal body weight, causing hypothermia, sedation and inducing catalepsy. The compounds therefore exhibit properties characteristic of anti-psychotic agents, for example, neuroleptics, and are therefore useful as anti-psychotic agents.

For these uses, the dosage will, of course, vary depending on the compound employed, mode of administration and treatment desired. However, in general, satisfactory results are obtained when administered at a daily dosage of from about 0.4 to about 60 mg/kg animal body weight, conveniently given in divided doses 2 to 4 times a day or in sustained release form. For the larger animals, the total daily dosage is in the range of from about 30 to about 350 mg, and dosage forms suitable for oral administration comprise from about 7 mg to about 175 mg of the compounds admixed with a solid or liquid pharmaceutical carrier or diluent.

The compounds may be administered in pharmaceutically acceptable salt forms, including acid addition salt forms, or in the form of complexes. Such forms exhibit the same order of activity as the free base forms and are readily prepared in conventional manner. Representative acids for acid addition salt forms include organic acids such as trifluoroacetic acid and mineral acids such as hydrochloric acid. Suitable metals for complex formation include zinc. The present invention also provides a pharmaceutical composition comprising a compound of formula I, in free base form or in the form of a pharmaceutically acceptable salt or complex, in association with a pharmaceutically acceptable carrier or diluent. Such compositions may be in the form of, for example, a solution or a capsule.

In one group of compounds, A is the residue as previously defined wherein R$_1$ and R$_2$ are as previously defined, R$_3$ is hydrogen whereby the hydroxy group is in the meta- or para-position to the —CH$_2$—CR$_1$NHZ—CO— residue, Z is hydrogen, alkyl of 1 to 5 carbon atoms, alkenyl of 3 to 5 carbon atoms, cyclopropylmethyl or cyclobutylmethyl, -Gly- or -(D)-Ala-, D is -Phe-, E is -(D)- or -(L)-methionine or -(D)- or -(L)-methionine-sulphoxide, F is —NR$_7$CHR$_8$CH$_2$OH wherein R$_7$ is hydrogen or alkyl of 1 to 4 carbon atoms,

TABLE

| | Compounds of formula H—Tyr—(D)-Ala—Gly—Phe—E—F | | | |
|---|---|---|---|---|
| Ex. No. | E—F | Salt Form | $[\alpha]_D^{22}$ | C |
| 4 | Methionine-asparaginol | TFA | −2.1° | 0.33% in DMF |
| 5 | Methionine-3-aminobutyrolactone | TFA | −14.8° | 0.27% in DMF |
| 6 | Methionine-glutaminol | TFA | −3.0° | 0.4% in DMF |
| 7 | Methionine-threoninol | TFA | +4.7° | 1% in DMF |
| 8 | Methioninesulphoxide-threoninol | TFA | +25.6° | 1.07% in AcOH 95% |
| 9 | Methioninesulphoxide-asparaginol | TFA | +12.8° | 1.1% in AcOH 95% |
| 10 | Methioninesulphoxide-glutaminol | TFA | +18.5° | 0.93% in AcOH 95% |
| 11 | Methioninesulphoxide-3-animo-butyrolactone | TFA | +4.5° | 0.94% in AcOH 95% |

The compounds of formula I are useful because they possess pharmacological activity in animals. In particular, the compounds are useful as analgesic agents for the treatment of pain as indicated in standard tests, e.g. by R$_8$ is as previously defined under (a), (b), (c), (d), (f) other than —(CH$_2$)$_4$—NHCOR$_4$, (g), (h);

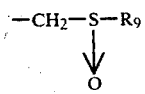

wherein R₉ is as previously defined,

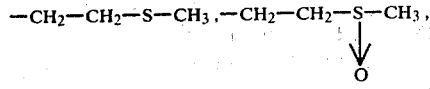

whereby A and D possess the (L)-configuration and F possesses either the (D)- or (L)-configuration.

In a second group of compounds, A is the residue as previously defined wherein $R_1$ and $R_2$ are as previously defined, $R_3$ is $R_4CO—$ which is in the meta- or para-position to the $—CH_2—CR_1NHZCO—$ residue, Z is hydrogen, alkyl of 1 to 5 carbon atoms, alkenyl of 3 to 5 carbon atoms, cyclopropylmethyl, cyclobutylmethyl or $R_4CO—$, B is -Gly- or -(D)-Ala-, D is -Phe- or -(D)-Phe-, E is -(D)- or (L)-methionine or (D)- or -(L)-methioninesulphoxide, F is $—NR_7CHR_8CH_2COR_4$ wherein $R_4$ is as previously defined, $R_7$ is hydrogen or methyl and $R_8$ is as previously defined under (a), (d), (g), (h); $—(CH_2)_m—CH_2COR_4$ wherein $R_4$ is as previously defined and m is from 0 to 6, $—CHCH_3COR_4$,

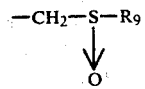

wherein R₉ is as previously defined,

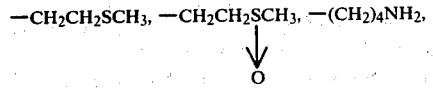

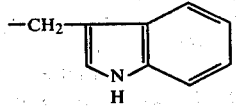

or; when Z is other than R₄CO;

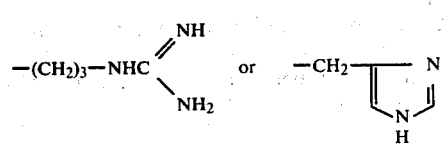

whereby A and D possess the (L)-configuration and F possesses the (D)- or (L)-configuration.

In a third group of compounds, A is the residue as previously defined wherein $R_1$ and $R_2$ are as previously defined, $R_3$ is $R_3'$ as previously defined whereby the $R_3'O$ group is in the meta- or para-position to the $—CH_2CR_1NHZCO—$ residue, Z is hydrogen, alkyl of 1 to 5 carbon atoms, alkenyl of 3 to 5 carbon atoms, cyclopropylmethyl, cyclobutylmethyl or $R_4CO—$ as previously defined, B is -Gly- or -(D)-Ala-, D is -Phe- or -(D)-Phe, E is -(D)- or (L)-methioninesulphoxide, F is $—NR_7CHR_8CH_2OR_3'$, wherein $R_3'$ is as previously defined, $R_7$ is hydrogen or methyl and $R_8$ is as previously defined under (a), (b), (c), (f) other than $—(CH_2)_4—NHCOR_4$, (g), (h);

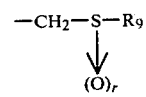

wherein R₉ is as previously defined, $—CH_2CH_2—S—CH_3$,
↓
O whereby A and D possess the (L)-configuration and F possesses the (D)- or (L)-configuration.

In a fourth group of compounds, A is the residue as previously defined, $R_1$ and $R_2$ are as previously defined, $R_3$ is $R_3'$ as previously defined whereby the $R_3'O$— group is in the meta- or para-position to the $—CH_2CR_1NHZCO—$ residue, Z is hydrogen, alkyl of 1 to 5 carbon atoms, alkenyl of 3 to 5 carbon atoms, cyclopropylmethyl, cyclobutylmethyl or $R_4CO—$, B is -Gly- or -(D)-Ala, D is the residue as previously defined wherein $R_5$ is hydrogen or methyl, $R_6$ is fluorine, chlorine, bromine, nitro, alkyl of 1 to 4 carbon atoms or alkoxy of 1 to 4 carbon atoms and z is 1 or 2, E is -(D)- or -(L)-methioninesulphone, -(D)- or -(L)-methioninesulphoxide or (D)- or -(L)-methionine, F is $—NR_7CHR_8CH_2OR_3'$ wherein $R_3'$ is as previously defined, $R_7$ is hydrogen or methyl and $R_8$ is as previously defined under (a), (b), (c), (f) other than $—(CH_2)_4—NHCOR_4$, (g), (h);

$—CH_2—S—R_9$
↓
$(O)_r$ wherein r and R₉ are as previously defined, $—CH_2CH_2—S—CH_3$
↓
$(O)_r$ wherein r is as previously defined or a residue as hereinbefore defined under (2°) wherein $R_7$ is hydrogen, whereby the A and D residues possess the (L)-configuration and the residue F possesses the (D)- or (L)-configuration.

What is claimed is:

1. A compound of the formula

A-B-Gly-D-E-F in which A is

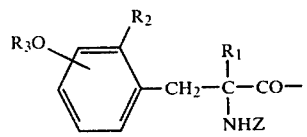

wherein
R₁ is hydrogen or methyl,
R₂ is hydrogen,
R₃ is hydrogen or methyl,
Z is hydrogen or methyl,
B is -(D)-Ala-,
D is a residue of formula $$\begin{array}{c} N-CH-CO- \\ | \quad | \\ R_5 \quad CH_2 \\ | \\ \text{(phenyl)} \\ | \\ (R_6)_z \end{array}$$

wherein
R₅ is hydrogen or methyl,
R₆ is hydrogen, chlorine, or nitro
E is -Leu- and Z is 1 or 2, $$CH_3-S(O)_r-(CH_2)_s-CH_2-CH\begin{array}{c}NH- \\ \\ CO\end{array}$$

wherein
r is 0, 1 or 2 and
s is 1, and
F is $$\begin{array}{c}-N-CH-CH_2OR_3', \\ | \quad | \\ R_7 \quad R_8\end{array}$$

wherein
R₃' is hydrogen
R₇ is hydrogen, and
R₈ is
(a) —CH₂OH
(b)

$$\begin{array}{c}-CH-OH \\ | \\ CH_3\end{array}$$

(c) —(CH₂)ₙ—CONH₂, wherein n is 1 or 2, or
(d)

$$\begin{array}{c}-NH-CH_2-CH_2 \\ | \quad \quad \quad | \\ CH_2 \quad \quad O \\ \quad \diagdown \; C \; \diagup \\ \quad \quad \| \\ \quad \quad O\end{array}$$

whereby the A, D and E residues possess either the L- or D,L- configuration and the residue F possesses the L-, D- or D,L- configuration,
or a pharmaceutically acceptable salt or complex form thereof.

2. A compound of claim 1 having the formula
H-Tyr-(D)-Ala-Gly-D-E-F where
D is phenylalanine or N-methylphenylalanine
E is leuine, methionine or methioninesulphoxide and
F is serinol, asparaginol, glutaminol, threonol or 3-aminobutyrolactone.

3. The compound of claim 1 which is H-Try-(D)-Ala-Gly-Phe-Met-serinol.

4. A compound of claim 1 which is H-Tyr-(D)-Ala-Gly-Phe-methioninesulphoxide-serinol.

5. A compound of claim 1 which is H-Tyr-(D)-Ala-Gly-MePhe-Leu-Asn-ol.

6. A compound of claim 1 which is H-Tyr-(D)-Ala-Gly-Phe-methionine-asparaginol.

7. A compound of claim 1 which is H-Tyr-(D)-Ala-Gly-Phe-methionine-3-aminobutyrolactone.

8. A compound of claim 1 which is H-Tyr-(D)-Ala-Gly-Phe-methionine-glutaminol.

9. A compound of claim 1 which is H-Tyr-(D)-Ala-Gly-Phe-methioninesulphoxide-threoninol.

10. A compound of claim 1 which is H-Tyr-(D)-Ala-Gly-Phe-methioninesulphoxide-asparaginol.

11. A compound of claim 1 which is H-Tyr-(D)-Ala-Gly-Phe-methioninesulphoxide-glutaminol.

12. A compound of claim 1 which is H-Tyr-(D)-Ala-Gly-Phe-methioninesulphoxide-3-aminobutyrolactone.

13. H-Tyr-(D)-Ala-Gly-Phe-Met-threoninol.

14. A pharmaceutical composition for treating pain and neuroleptic condition in animals comprising an effective amount a compound of claim 1, in association with a pharmaceutically acceptable carrier or diluent.

15. A method of treating pains in animals, which comprises administering to an animal in need of such treatment, a therapeutically effective amount of a compound of claim 1.

16. A method of treating neuroleptic conditions in animals, which comprises administering to an animal in need of such treatment, a therapeutically effective amount of a compound of claim 1.

* * * * *